(12) United States Patent
Goldsmith et al.

(10) Patent No.: US 7,133,879 B1
(45) Date of Patent: Nov. 7, 2006

(54) PERSONALIZED LIBRARY INTERFACE FOR PROVIDING DATA TO A USER

(75) Inventors: Brian Goldsmith, Folsom, CA (US); Alan G Maloney, San Francisco, CA (US)

(73) Assignee: CogentMedicine, Inc., San Francisco, CA (US)

( * ) Notice: Subject to any disclaimer, the term of this patent is extended or adjusted under 35 U.S.C. 154(b) by 466 days.

(21) Appl. No.: 10/330,648

(22) Filed: Dec. 27, 2002

Related U.S. Application Data

(60) Provisional application No. 60/343,966, filed on Dec. 28, 2001.

(51) Int. Cl.
*G06F 17/30* (2006.01)

(52) U.S. Cl. ............... 707/102; 707/100; 707/101; 707/103 R; 707/104.1; 707/2

(58) Field of Classification Search ............ 707/2, 707/100, 101, 102, 103 R, 104.1
See application file for complete search history.

(56) References Cited

U.S. PATENT DOCUMENTS

| | | | |
|---|---|---|---|
| 6,473,794 B1 * | 10/2002 | Guheen et al. ............ 709/223 |
| 6,519,571 B1 * | 2/2003 | Guheen et al. ............ 705/14 |
| 6,536,037 B1 * | 3/2003 | Guheen et al. ............ 717/151 |
| 6,560,588 B1 * | 5/2003 | Minter ............ 706/50 |
| 6,606,744 B1 * | 8/2003 | Mikurak ............ 717/174 |
| 6,615,166 B1 * | 9/2003 | Guheen et al. ............ 703/27 |
| 6,647,383 B1 * | 11/2003 | August et al. ............ 707/3 |
| 6,671,818 B1 * | 12/2003 | Mikurak ............ 714/4 |
| 6,721,713 B1 * | 4/2004 | Guheen et al. ............ 705/1 |
| 6,792,399 B1 * | 9/2004 | Phillips et al. ............ 705/36 R |
| 6,868,525 B1 * | 3/2005 | Szabo ............ 715/738 |
| 6,957,186 B1 * | 10/2005 | Guheen et al. ............ 705/1 |
| 2004/0064351 A1 * | 4/2004 | Mikurak ............ 705/7 |
| 2004/0107125 A1 * | 6/2004 | Guheen et al. ............ 705/7 |

* cited by examiner

*Primary Examiner*—Frantz Coby
(74) *Attorney, Agent, or Firm*—Wilson Sonsini Goodrich & Rosati

(57) ABSTRACT

A personalized library interface that can be modified by a user and provides and that allows access to one or more data sets. A user indicates search strategies, and access to stored preselections is provided. Depending on user indication, the user is provided with information relevant to the search strategy or to information preselected by an entity other than a user, for example, an expert or advertiser. Searches from other entities may also be saved and used as an interface to the data sets.

21 Claims, 6 Drawing Sheets

PERSONALIZED LIBRARY INTERFACE FOR PROVIDING DATA TO A USER

CROSS REFERENCE TO RELATED APPLICATIONS

This application claims priority from U.S. Provisional Patent Application Ser. No. 60/343,966, filed Dec. 28, 2001, the contents of which are incorporated herein by reference.

FIELD OF THE INVENTION

The present invention relates generally to the organization of data for presentation to a computer user. More particularly, the present invention relates to methods for organizing the presentation of data to a user via a website or other computer display by creating a personalized library interface to data sets.

BACKGROUND OF THE INVENTION

Technological advances in computer storage and processing has led to the availability of large sets of data. Such data sets may be continuously updated or added to as new data is generated. Data sets may be proprietary, such as the MEDLINE database (from the National Library of Medicine), the LEXIS/NEXIS data set, or any private corporate database (such as an internal database of documents). A data set may also be public, such as a database of government records or filings.

Computer users often wish to search through data sets. In order to search this data, in some systems, users may enter search strategies and review the documents that match the search strategies inputted. However, it is time-consuming and, depending on the user's costs for accessing the data set, may be costly for a user to find data of interest. Thus, there is a need for an improved method and system for allowing user access to a data in a database.

SUMMARY OF THE INVENTION

The present invention is a method of presenting data to the user that allows the user improved flexibility and ease of use in searching data sets. It creates a personalized library for a user, provides access to that library, and provides for automatic updating of the library and for user use and modification of the library.

The present invention provides a user with the ability to enter searches for one or more data sets and accepts user requests to view data. Based on the user request, the invention will provide the user with data corresponding to the user-entered search or with data preselected by an entity other than the user. This entity may be an entity who has reviewed data and preselected data for a particular topic or area of interest (an "editor" or "expert"). The entity may be an advertiser who presents data from the data set which relates to the advertiser's product or service.

BRIEF DESCRIPTION OF THE DRAWINGS

The above and other benefits and advantages of the invention will be apparent from the following detailed description, of which.

DETAILED DESCRIPTION OF ILLUSTRATIVE EMBODIMENTS

The invention comprises systems and methods for providing information to a user via a computer. The information may be resident on the user's computer or may be remote to it. The information may be proprietary to an information provider, and access to some or all of the information may be restricted based on payments or user login. In one embodiment, the invention is implemented using a web browser.

The invention provides access to one or more databases to a user. The user can select areas of interest and store searches to be performed on the databases. Additionally, the user can access data selections made by an entity other than the user. For example, the user can request data selections regarding a specified topic made by an expert in that topic. The user can request data selections made by an advertiser.

Access to the data selections depends on the underlying databases. For example, the database may provide only a data identifier (such as citation information for an article) for a data item and charge a cost for viewing the entire item (e.g. the article). In one embodiment, the invention provides password and payment management for the databases as necessary.

In one embodiment, the method of the invention provides four different types of data folders. These data folders are used to access information from one or more data sets. This information is selected for inclusion into the folder by the user, by another person, or by a search (such as a keyword search or concept search performed on the data set.) Either full information from the data set or summary information (such as citation information) is available. A fifth folder type is organizational, used to create a hierarchy of data of different types. A user navigates organizational folders by, for example, creating, deleting, opening, closing, and moving them. Within data folders, the user is presented with data and the means to manipulate data.

Figure 1:
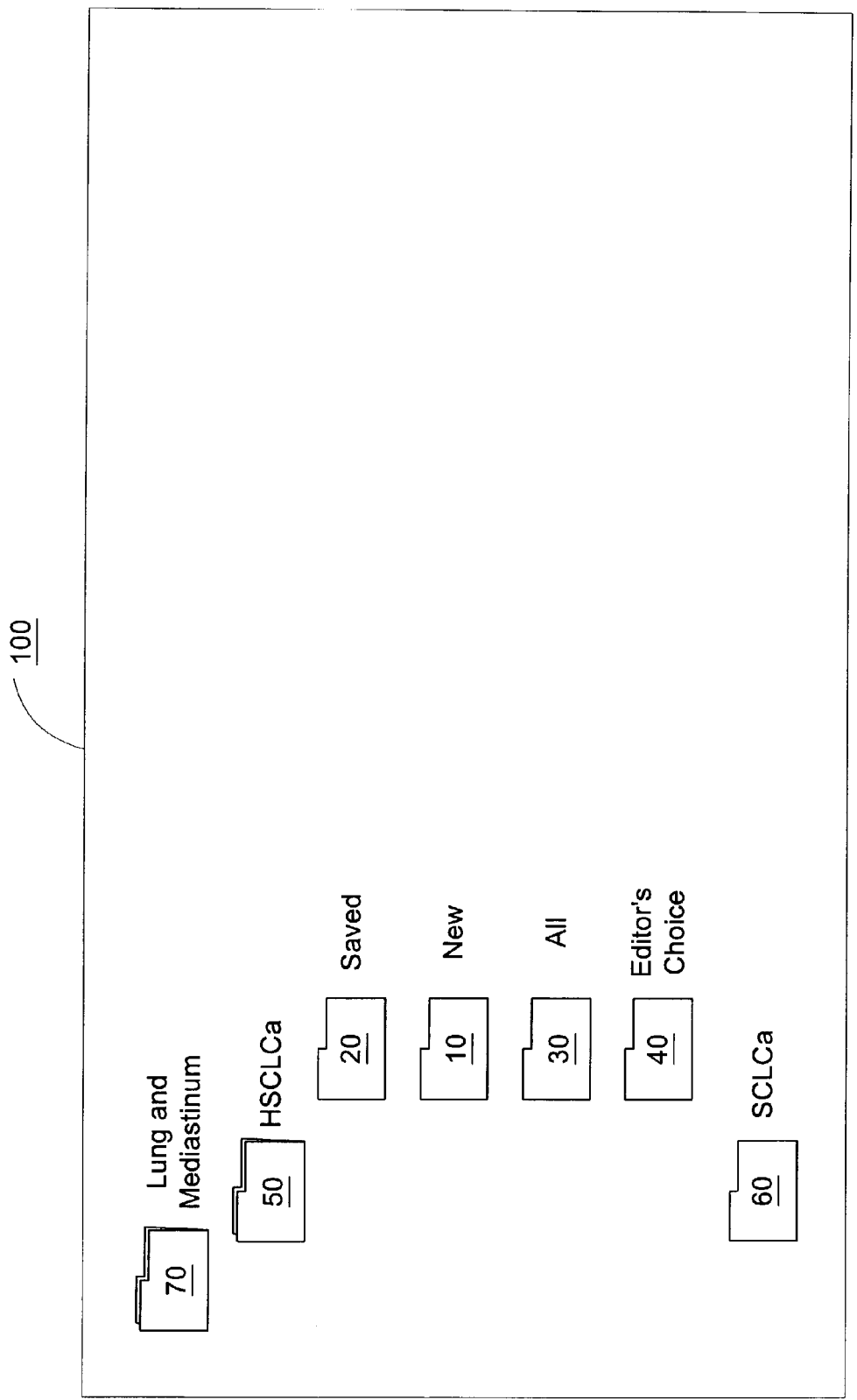
FIG. 1 depicts an illustrative user interface display for use with a Web site in accordance with one embodiment of the present invention.

As shown in FIG. 1, the user's display area 100 is used to display information to the user, including folder information. In FIG. 1, a new-citations folder 10, saved-folder 20, all-citations folder 30 and editor's-choice folder 40 are all contained in an organizational folder labeled NSCLCa (non-small cell lung cancer) 50. This organizational folder, along with one labeled SCLCa (small cell lung cancer) 60, is itself contained in an organizational folder labeled Lung and Mediastinum 70. Thus, a hierarchy of folders is created. A user can navigate this hierarchy to find or create an organizational folder or a data folder for data the user wishes to view.

In new-citations folder 10, a user may enter one or more search strategies and associate them with one or more data sets. The search strategies are run on the data sets, and the results, comprising identifiers for any recent documents (in one embodiment, documents less than one week old), are stored in the folder or run when the folder is opened. Search strategies are saved in data structures for repeat use by the user. In another embodiment, documents stored in the new-citations folder are documents which have been added to the data set(s) since the last time the user accessed the new-citations folder. When the user opens the folder, the user is presented with these identifiers. For example, if the system was linked to the MEDLINE database, when the new-citations folder is opened, citations for the MEDLINE data for articles which match the search criteria and the recency criteria would be displayed. According to one embodiment of the invention, the search is done when a folder is opened, in other embodiments searches are batched and may be performed before a folder is opened or at some point after a user identifies folders to populate with data.

An identifier, which may be data set-dependent, may consist of the title, author, publication, synopsis, or even the complete document. In one embodiment, it consists of the first three authors of a document, the title, source, synopsis, and a data set identifier. Where it is not the complete document, an identifier, in one embodiment, is easily used (by clicking with a mouse or selecting with the keyboard) to obtain the complete document. If this necessitates user password or other account information (for example, a user id and password or payment information) this will be automated when the user requests the complete document.

Optionally, the user is given assistance in formulating a search, and logic is used that allows one search to be used on multiple data sets even where the sets use different search languages or formats.

With reference to FIG. 1, a second type of data folder that may be presented to the user is an "all-citations" folder 30. All-citations folder 30 also uses one or more search strategies and one or more data sets; however, the results are not limited in time to the most recent documents. An all-citations folder may be associated with a "new citations" folder so that they share common search strategy and data set information. In this way, the user need only enter one or more search strategies and associate them with one or more data sets once, and two folders, the new-citation and the all-citation folders are created.

A third type of folder is "saved-folder" 20. Saved-folder 20 stores identifiers used by the user as a personal library of documents. When a user finds an identifier or a document that the user deems important, the user may place the identifier(s) or document(s) into the saved-folder. This allows the user to store documents in one place, so that their review of information in all-citations or new-citations folders may be stored in one location. In one embodiment, the user may annotate the identifier or document to indicate further information regarding the selection.

Figure 2:
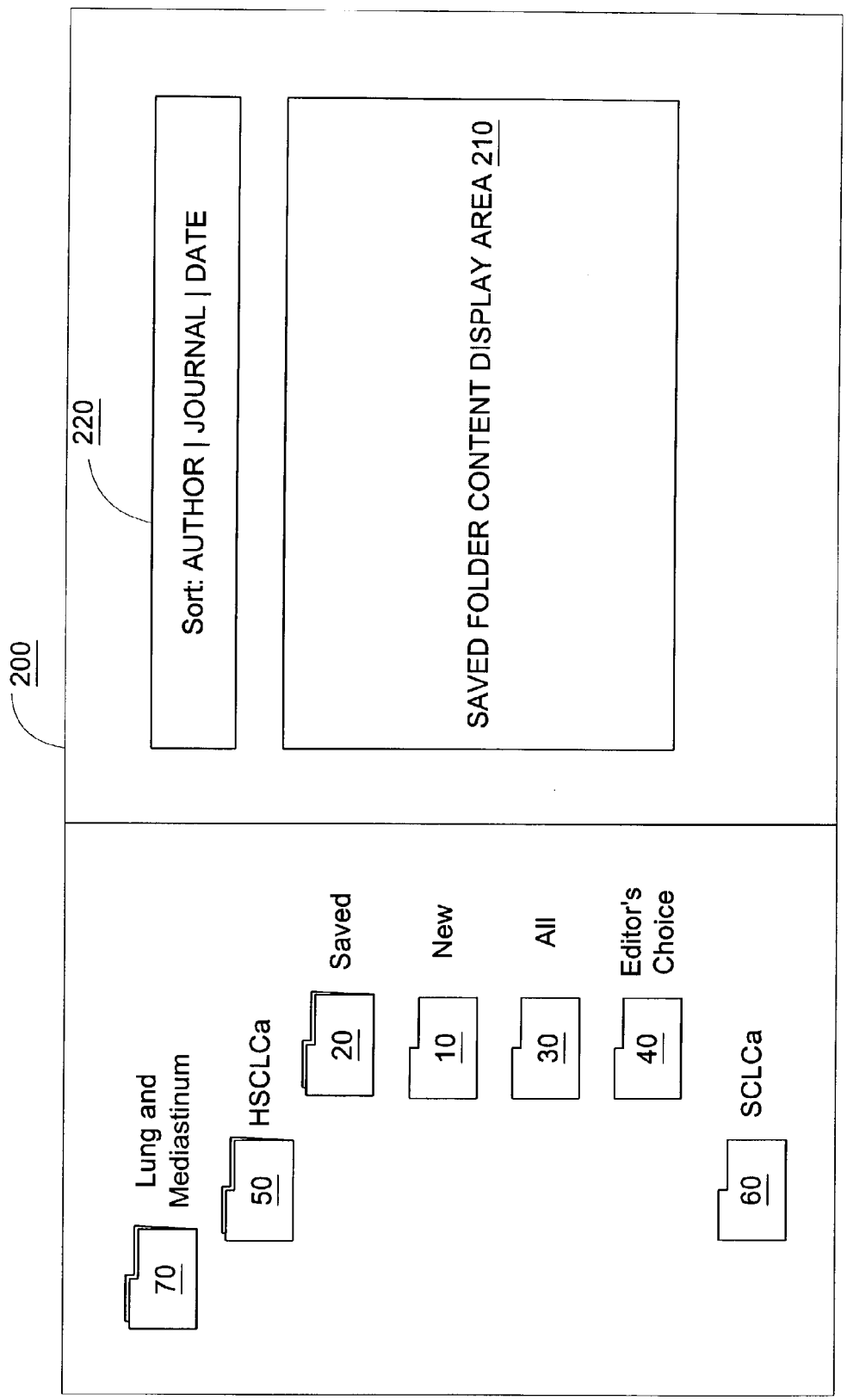
FIG. 2 depicts an illustrative user interface display with an open saved-folder for use with a Web site in accordance with one embodiment of the present invention.

With reference to FIG. 2, the identifiers for the data in the open folder (saved folder 20) are displayed on the right side of the screen 200, in folder content display area 210. The identifiers can be sorted by author, journal, or date, by clicking on the text within the sorting links area 220, and the first three authors, title, and bibliographic information is given for each article in saved folder 20. When other information is included in the identifier, this may also be used for the sort in sorting links area 220.

Different saved-folders (or subfolders of a main saved-folder) may be used for different projects or areas of research or data. In one embodiment, folders may also be shared with other users. In one embodiment, such sharing is subject to rules concerning the two users and the data sets from which the information is derived (so that users are not sharing information in violation of agreements regarding the use of the data sets). In FIG. 2, the saved-folder 20 is open. Contents of the folder are displayed in saved folder content display area 210 which continues in the window and the remainder of which is viewable by scrolling down in the window or following links to continuation areas.

Figure 3:
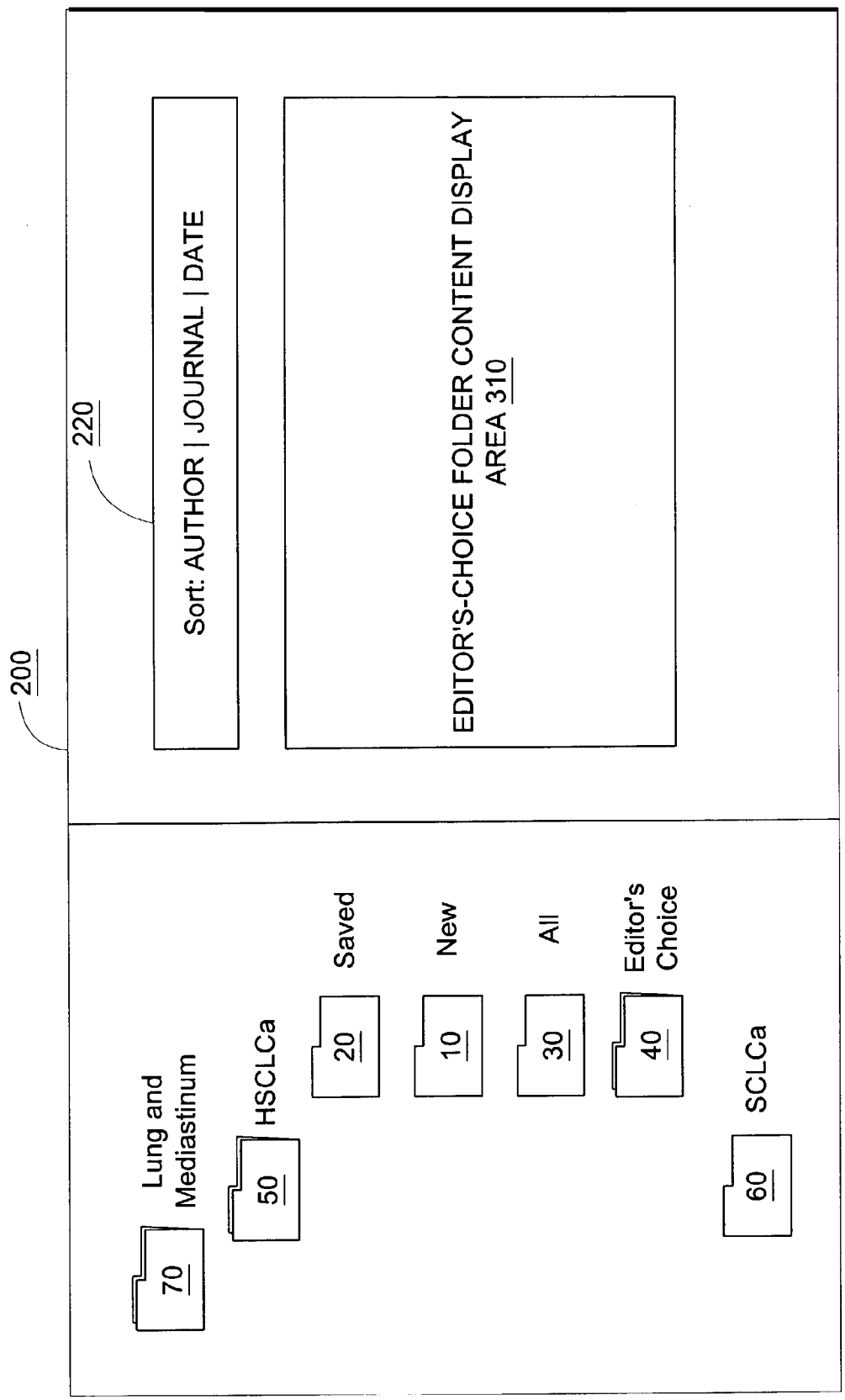
FIG. 3 depicts an illustrative user interface display with an open editor's-choice folder for use with a Web site in accordance with one embodiment of the present invention.

A fourth type of folder present in this embodiment is an "editor's-choice folder" 40. In editor's folder 40 an editor, for example, a specialist in a field or an AI program, can review information from the data sets and place documents or identifiers that the editor selects for a specific user or users in a specific editor's-choice folder. For example, if the data set is medical information, and the user is a medical professional, the editor may be a specialist in a specific area who reviews information from a medical data set and places certain documents or identifiers of specific interest to the user or users into an editor's folder. This can be seen as similar to a saved-folder, except that, in this embodiment, the user does not have the ability to select or modify the selections in the editor's-choice folder. In FIG. 3, the editor's-choice folder 40 is open and the contents will be displayed in editor's-choice folder content display area 310. Editor's-choice folder content display area 310 may be a window with scrolling, and if not all content can be viewed at once, it is viewable by scrolling down in the window or following links to continuation areas.

In addition to an expert, an advertiser or any other third-party may choose to make an editor's-choice folder available to users. In this way, a third-party's work in selecting content from one or more databases is accessible to the user.

Organizational folders include folders selected by a user or automatically generated to correspond to a specific type (for example, all folders with data from a specific data set, or all folders with names including a specified keyword). A folder may then be in several organizational folders. Organizational folders may be in other organizational folders. So a user may go to a folder about a broad topic, and find inside folders about narrow subtopics, and inside one of these folders may find, e.g., two saved-folders, two new-citations folders containing up-to-date results of a saved search strategy, an editor's-choice folder, and an all-citations folder containing the search in one of the new-folders (but including material that may be older than the material in that folder.)

Inside folders, documents or identifiers may be organized in a number of different ways. For example, where identifiers include author, journal, and date information, documents may be organized according to any of these types of information. Where other information is included in the data set or identifiers for the folder, that other information may be used for organization. The organization of the information displayed can be changed as described above.

Figure 4:
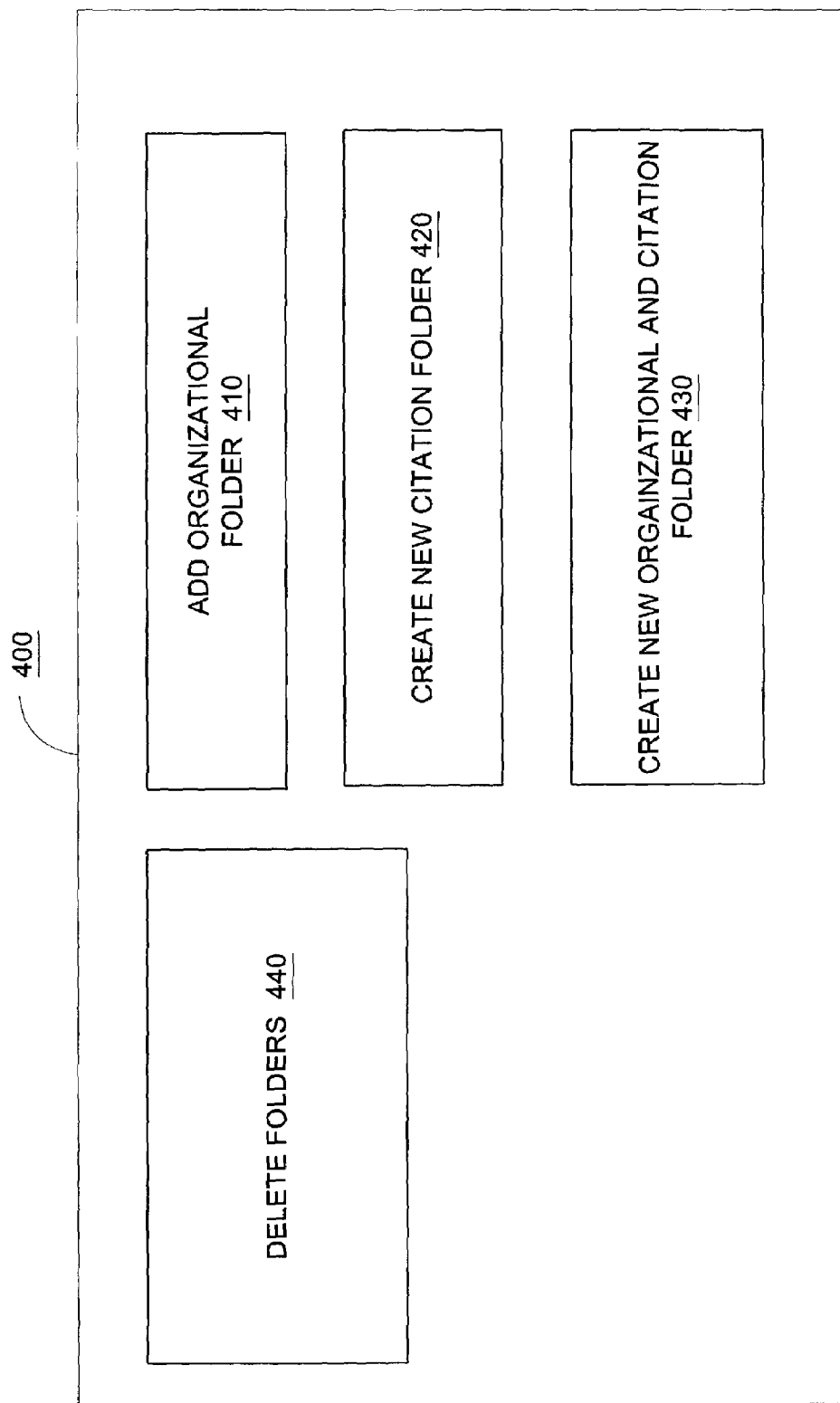
FIG. 4 depicts an illustrative user interface display with folder tools for use with a Web site in accordance with one embodiment of the present invention.

The user is assisted in the construction of folders as shown in FIG. 4, in the folder options screen 400. The user may select an organizational folder to add in the add organizational folder area 410. In this area, default organizational folders are listed. Organizational folders may be selected for addition to a user's organizational folders. In order to switch between screens, according to one embodiment, a link is presented for the user to select. In other embodiments, pull-down menus or alternate means are used to change screens.

In the create citation folder area 420, a user can create a sub-folders for an organizational folder. The user is presented with a list of existing organizational folders, and the user can create a sub-folder and name the sub-folder in this area. Another area, the new organizational and citation folders area 430 can be used to add folders on more than one level at once. Folders can also be deleted in delete folders area 440. All folders are listed, and folders selected for deletion by selecting one or more folders for deletion. Folder creation may be accomplished by navigating the folder hierarchy and selecting where new folders should be created or selecting folders for deletion. For each user, the current folder hierarchy and searches are saved so that the user's information is presented to the user each time the invention is used.

In one embodiment, the user display may include additional information, such as advertising information, which can be used to create folders. For example, in the medical information context, this advertising information may be a clickable banner ad for a specific pharmaceutical. When the user clicks on the banner ad, a folder is created for the user which contains citations related to the product or service advertised. Alternatively, clicking on such a banner ad causes one or more folder to be created which contains citations based on a product-related search strategy. In this way, an advertiser can provide information in the form of selected articles or a selected search strategy which allows a user to access information related to the advertiser's product or service. An advertiser may provide free access to the data items selected or to a database on which the search strategy is to be run. Alternately, the advertiser may simply provide a search strategy to be used in the same manner that user created searches and selections are used. In this way, the data may be presented to or made accessible to the user from an advertiser's computer system or data may be taken from one or more databases accessible to the user.

Figure 5:
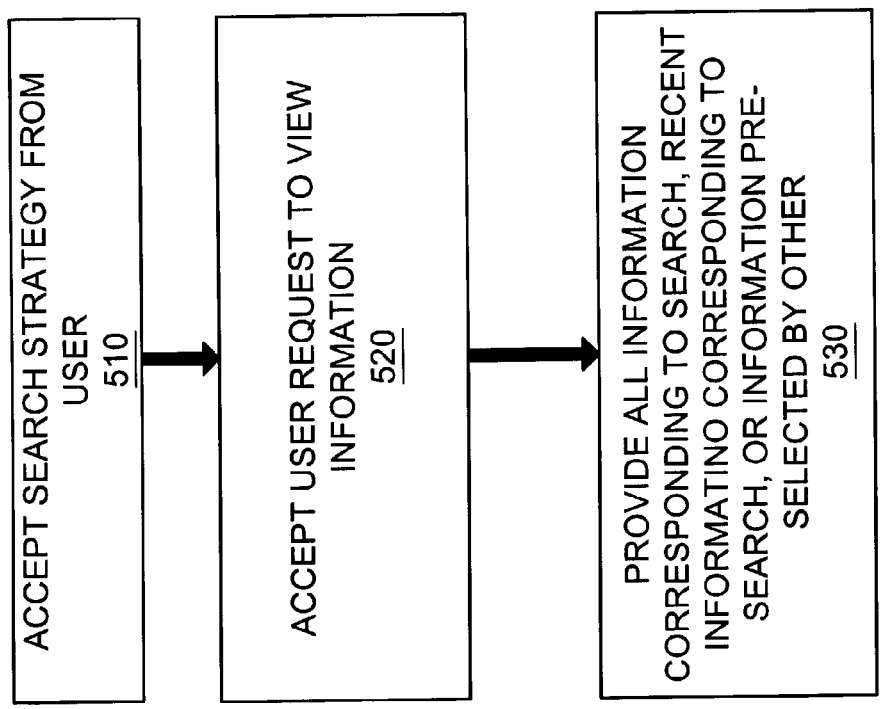
FIG. 5 depicts a method for displaying data to a user corresponding to one embodiment of the present invention.

As has been described, search strategies may be accepted from a user and provided along with data set information preselected by another entity, such as an expert or advertiser. As shown in FIG. 5, one or more search strategies are accepted from the user in step 510. These one or more search strategies can be associated with different data sets. In step 520, a user request to view information is accepted. In step 530, the user is provided with recent information corresponding to a search strategy, all information corresponding to a search strategy, or information pre-selected by an entity other than the user.

Figure 6:
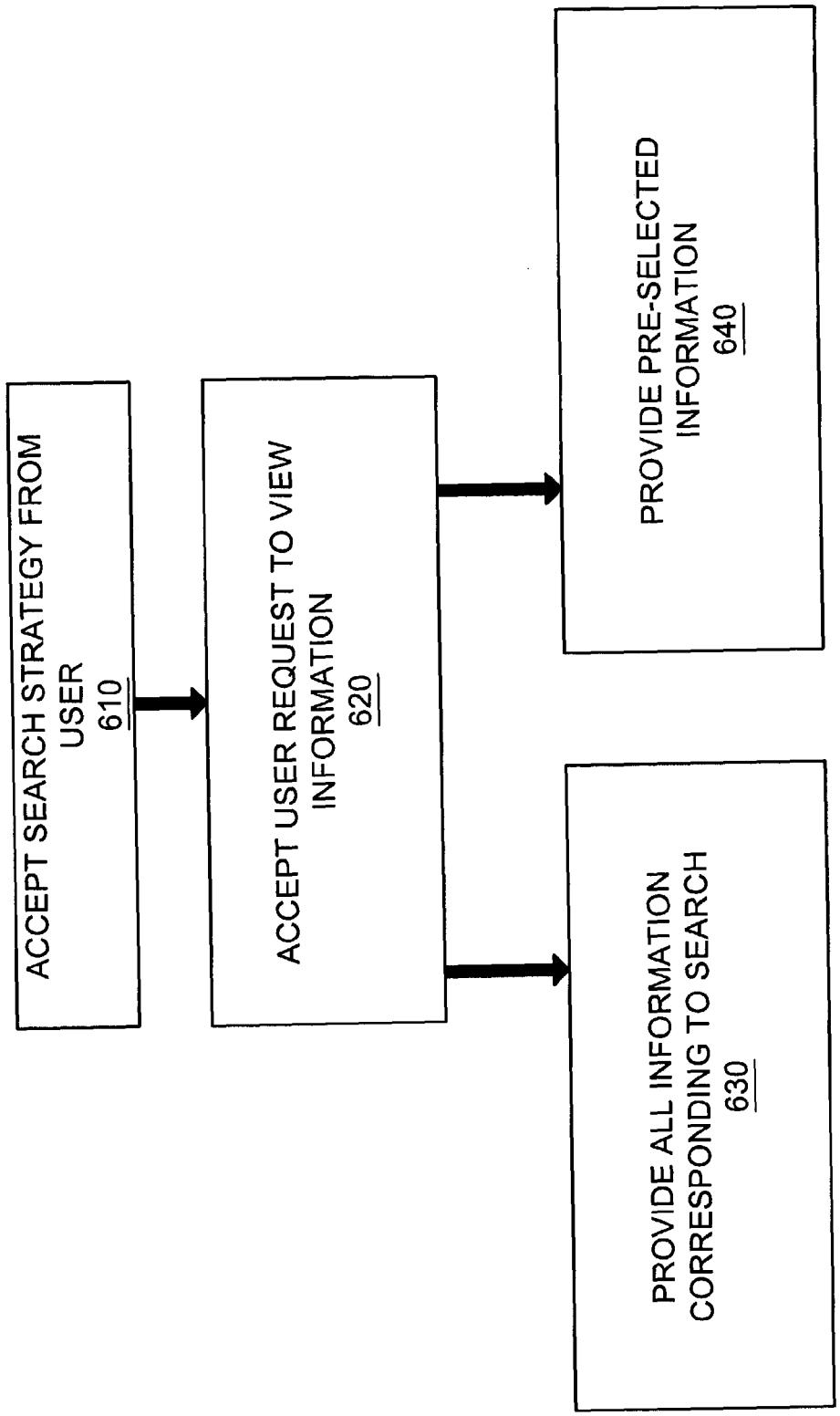
FIG. 6 depicts a method for displaying data to a user corresponding to another embodiment of the present invention.

In another implementation, the user can access a user saved folder, which contains saved searches and/or saved documents or identifiers, and an editor folder, which contains editor-selected documents. As shown in FIG. 6, step 610, one or more search strategies are accepted from a user in step 610. A user request to view information is provided in step 620. Based on that request, information is presented to the user. In step 630, information corresponding to a search strategy is presented to the user, and in step 640, preselected information is provided to the user.

A computer system can be used according to the invention. A user interface, such as a keyboard, a touchscreen, or a mouse in combination with a display may be used to interact with the user. Computer storage may store hierarchy and search information. Information is accepted from the user from a user input means, such as a keyboard or mouse. And a display is used to display information to a user. Other display means, such as a printer, may also be used. Data may be stored for later display.

Thus, there has been described a method and system for providing data to a user. Those skilled in the art will appreciate that numerous changes and modifications may be made to the preferred embodiments of the invention, for example, that "folders" do not imply any specific data structure or visual representation, that data may be stored in memory and accessed in any data structure which is convenient, and that such changes and modifications may be made without departing from the spirit of the invention. It is therefore intended that the appended claims cover all such equivalent variations as fall within the true spirit and scope of the invention.

We claim:

1. A method for providing data to a user from one or more data sets, said method comprising:

accepting from a user and storing one or more search strategies directed to medical literature in data folders wherein said storage is for repeat use by a user, each of said one or more search strategies associated with one or more of said one or more data sets; and accepting from said user a request to view medical information, and, based on said request, selectively providing data set information in said data folders comprising preselected medical information for said user or users from said one or more data sets, said medical information having been preselected and placed in said folder by a specialist for said user or users and at least one of (a) medical information from said one or more associated data sets corresponding to one of said search strategies directed to medical literature wherein said medical information is added to the said one or more data sets since the last time said user accessed said one or more associated data sets; or (b) medical information corresponding to one of said search strategies directed to medical literature wherein said medical information is not limited in time.

2. The method of claim 1, where said method further comprises:

accepting from said user one or more selected document identifiers or documents from said one or more data sets and storing these identifiers or documents;

accepting from said user a request to view information from said user stored selected documents, and providing said user stored selected documents.

3. The method of claim 1, where said preselected information is preselected by an expert.

4. The method of claim 1, where said preselected information is preselected by an advertiser.

5. The method of claim 1, where said method further comprises:

storing one or more search strategies in said data folders developed by said specialist wherein each of said one or more search strategies is associated with one or more of said one or more data sets;

accepting from said user a request to view search information in said data folders by said specialist, and selectively providing data set information in said data folders comprising at least one of (a) medical information from said one or more associated data sets corresponding to one of said search strategies wherein said medical information is added to the said one or more data sets since the last time said user accessed said one or more associated data sets; or (b) medical information corresponding to one of said search strategies wherein said medical information is not limited in time.

6. The method of claim 5, where said one or more search strategies are provided by an expert.

7. The method of claim 5, where said one or more search strategies are provided by an advertiser.

8. The method of claim 1, where said data set information comprises identifier information for one or more data items from said one or more data sets.

9. The method of claim 8, where said identifier information comprises citation information.

10. The method of claim 1, where said data set information comprises one or more data items from said one or more data sets.

11. At least one of an operating system, a computer-readable medium having stored thereon a plurality of computer-executable instructions, a co-processing device, and, a computing device for performing the method of claim 1.

12. A system for providing data to a user, comprising:
   user interface and storage means for accepting from a user and storing one or more search strategies directed to medical literature, each of said one or more search strategies associated with one or more of said one or more data sets; and
   user input and display means for accepting from said user a request to view medical information, and based on said request, selectively providing data set information in data folders comprising preselected medical information for said user or users from said one or more data sets, said medical information having been preselected and placed in said folder by a specialist for said user or users and
   at least one of (a) medical information from said one or more associated data sets corresponding to one of said search strategies directed to medical literature wherein said medical information is added to the said one or more data sets since the last time said user accessed said one or more associated data sets; or (b) medical information corresponding to one of said search strategies directed to medical literature wherein said medical information is not limited in time.

13. A method for providing data to a user from one or more data sets, said method comprising:
   accepting from a user and storing one or more search strategies directed to medical literature, each of said one or more search strategies associated with one or more of said one or more data sets;
   accepting from a user a request to view medical information;
   providing data set information in data folders comprising medical information from said one or more associated data sets corresponding to one of said search strategies directed to medical literature; and
   providing data set information in data folders comprising preselected medical information for said user or users from said one or more data sets, said medical information having been preselected and placed in said folder by a specialist for said user or users.

14. The method of claim 13, where said preselected information is preselected by an expert.

15. The method of claim 13, where said preselected information is preselected by an advertiser.

16. The method of claim 13, where said method further comprises:
   storing one or more search strategies in said data folders developed by said specialist wherein each of said one or more search strategies is associated with one or more of said one or more data sets;
   accepting from said user a request to view search information in said data folders by said specialist, and selectively providing data set information in said data folders comprising at least one of (a) information from said one or more associated data sets corresponding to one of said search strategies wherein said medical information is added to the said one or more data sets since the last time said user accessed said one or more associated data sets; or (b) medical information corresponding to one of said search strategies wherein said medical information is not limited in time.

17. The method of claim 16, where said one or more search strategies are provided by an expert.

18. The method of claim 16, where said one or more search strategies are provided by an advertiser.

19. The method of claim 13, where said data set information comprises identifier information for one or more data items from said one or more data sets.

20. At least one of an operating system, a computer-readable medium having stored thereon a plurality of computer-executable instructions, a co-processing device, and, a computing device for performing the method of claim 13.

21. A system for providing data to a user, comprising:
   user interface and storage means for accepting from a user and storing one or more search strategies directed to medical literature, each of said one or more search strategies associated with one or more of said one or more data sets;
   data input means for accepting from a user a request to view medical information;
   display means for providing data set information in data folders comprising medical information from said one or more associated data sets corresponding to one of said search strategies directed to medical literature; and
   display means for providing data set information in data folders comprising preselected medical information for said user or users from said one or more data sets said medical information having been preselected and placed in said folder by a specialist for said user or users.

* * * * *